(12) United States Patent
Mena Cervantes et al.

(10) Patent No.: US 10,442,981 B2
(45) Date of Patent: Oct. 15, 2019

(54) HYDROXYPROPYL BETAINE BASED ZWITTERIONIC GEMINAL LIQUIDS, OBTAINING PROCESS AND USE AS WETTABILITY MODIFIERS WITH INHIBITORY/DISPERSANTS PROPERTIES OF ASPHALTENES

(71) Applicant: INSTITUTO MEXICANO DEL PETRÓLEO, Mexico City (MX)

(72) Inventors: Violeta Yázmin Mena Cervantes, México, D.F. (MX); Raúl Hernández Altamirano, México, D.F. (MX); Luis Silvestre Zamudio Rivera, México, D.F. (MX); Alejandro Ramírez Estrada, México, D.F. (MX); Jorge Francisco Ramírez Pérez, México, D.F. (MX); José Manuel Martínez Magadan, México, D.F. (MX); Rodolfo Cisneros Devora, México, D.F. (MX)

(73) Assignee: INSTITUTO MEXICANO DEL PETRÓLEO, Mexico City (MX)

( * ) Notice: Subject to any disclaimer, the term of this patent is extended or adjusted under 35 U.S.C. 154(b) by 385 days.

(21) Appl. No.: 14/944,150

(22) Filed: Nov. 17, 2015

(65) Prior Publication Data

US 2016/0168447 A1 Jun. 16, 2016

(30) Foreign Application Priority Data

Dec. 11, 2014 (MX) .................. MX/a/2014/015224

(51) Int. Cl.
*C07C 309/14* (2006.01)
*C07C 303/22* (2006.01)
(Continued)

(52) U.S. Cl.
CPC ............ *C09K 8/584* (2013.01); *C07C 213/00* (2013.01); *C07C 227/16* (2013.01);
(Continued)

(58) Field of Classification Search
None
See application file for complete search history.

(56) References Cited

U.S. PATENT DOCUMENTS

| 3,643,738 A | 2/1972 | Dreher et al. |
| 4,509,951 A | 4/1985 | Knapp |

(Continued)

FOREIGN PATENT DOCUMENTS

MX 2010012348 A 5/2012

OTHER PUBLICATIONS

Fang et al., "The Knoevenagel reaction in water catalyzed by zwitterionic liquids", Chemical Monthly, published May 26, 2008, pp. 799-803, vol. 139, Springer-Verlag, The Netherlands.
(Continued)

*Primary Examiner* — Jeffrey D Washville
(74) *Attorney, Agent, or Firm* — Casimir Jones, S.C.; Anne Reynolds

(57) ABSTRACT

The present invention is related to the obtaining and use of zwitterionic geminal liquids based on hydroxypropyl betaine, as wettability modifiers of rocks such as limestone, dolomite, sandstone, quartz or heterogeneous lithologies, in the presence of brines with high content of divalent ions as calcium, magnesium, barium and strontium, at high temperature and high pressure conditions during the application of enhanced oil recovery processes.

The zwitterionic geminal liquids based hydroxypropyl betaine of the present invention have also the property of acting as inhibitors/dispersing of asphaltenes, both at extraction and production operations of petroleum industry, thus
(Continued)

a)

b)

allowing to increase the level of crude oil production. An additional advantage presented by zwitterionic geminal liquid based on hydroxypropyl betaine which can be dissolved in distilled water, brine, aliphatic hydrocarbons or other polar and nonpolar solvents.

27 Claims, 3 Drawing Sheets

(51) Int. Cl.
    *C09K 8/54*        (2006.01)
    *C09K 8/584*      (2006.01)
    *C09K 8/524*      (2006.01)
    *C10G 75/04*      (2006.01)
    *C07C 213/00*     (2006.01)
    *C07C 227/16*     (2006.01)
    *C07C 229/08*     (2006.01)

(52) U.S. Cl.
    CPC ............ *C07C 229/08* (2013.01); *C09K 8/524* (2013.01); *C10G 75/04* (2013.01)

(56) References Cited

U.S. PATENT DOCUMENTS

| | | |
|---|---|---|
| 4,842,065 A | 6/1989 | McClure |
| 5,021,498 A | 6/1991 | Stephenson et al. |
| 5,042,580 A | 8/1991 | Cullick et al. |
| 5,388,644 A | 2/1995 | Romocki |
| 5,466,387 A | 11/1995 | Planta et al. |
| 5,494,607 A * | 2/1996 | Manek et al. |
| 5,504,063 A | 4/1996 | Becker et al. |
| 6,048,904 A | 4/2000 | Wiehe et al. |
| 6,063,146 A | 5/2000 | Miller et al. |
| 6,180,683 B1 | 1/2001 | Miller et al. |
| 6,204,420 B1 | 3/2001 | Miller et al. |
| 6,313,367 B1 | 11/2001 | Breen |
| 6,946,524 B2 | 9/2005 | Breuer et al. |
| 7,097,759 B2 | 8/2006 | Mukkamala |
| 7,122,112 B2 | 10/2006 | Mukkamala et al. |
| 7,122,113 B2 | 10/2006 | Cornelisse |
| 2009/0023618 A1 | 1/2009 | Futterer et al. |
| 2011/0138683 A1* | 6/2011 | Hern ndez Altamirano ................ C07C 229/12 44/391 |
| 2011/0162558 A1 | 7/2011 | Mena Cervantes et al. |
| 2013/0296200 A1* | 11/2013 | Hernandez Altamirano ............... C09K 8/584 507/241 |

OTHER PUBLICATIONS

Yoshizawa et al., "A New Family of Zwitterionic Liquids Arising from a Phase Transition of Ammonium Inner Salts Containing an Ether Bond", Chemistry Letters, Aug. 27, 2004, pp. 1594-1595, vol. 33, No. 12, The Chemical Society of Japan, Tokyo, Japan.

Podjava et al., "Liquid Chromatography—Mass Spectrometry of Zwitterionic Liquids", Latvian Journal of Chemistry, 2010, pp. 102-113, No. 1-4, Department of Chemistry, University of Latvia, Riga, Latvia.

* cited by examiner a) b)

HYDROXYPROPYL BETAINE BASED ZWITTERIONIC GEMINAL LIQUIDS, OBTAINING PROCESS AND USE AS WETTABILITY MODIFIERS WITH INHIBITORY/DISPERSANTS PROPERTIES OF ASPHALTENES

CROSS-REFERENCE TO RELATED APPLICATION(S)

This claims priority to Mexican Patent Application No. MX/a/2014/015224, filed on Dec. 11, 2014, the entire contents of which are fully incorporated herein by reference.

TECHNICAL FIELD OF THE INVENTION

The present invention is situated in the field of multifunctional chemicals applied in the oil industry for enhanced recovery processes, it is specifically related to the obtaining and use of hydroxypropyl betaine based zwitterionic geminal liquids with wettability modifying properties on carbonate rocks and heterogeneous lithologies, in the presence of brines with high content of divalent ions such as calcium, magnesium, barium and strontium; high temperature and high pressure.

These zwitterionic liquids simultaneously exhibit the property of acting as inhibitors/dispersants of asphaltenes, both in extraction and production operations as well as in transport and storage operations, thus allowing increasing the recovery factor in crude oil production operations.

BACKGROUND OF THE INVENTION

Geminal zwitterionics liquids (1) constitute a chemical family characterized by possessing hydrocarbon chains (A), a bridge (B) and two zwitterionic type polar groups (C).

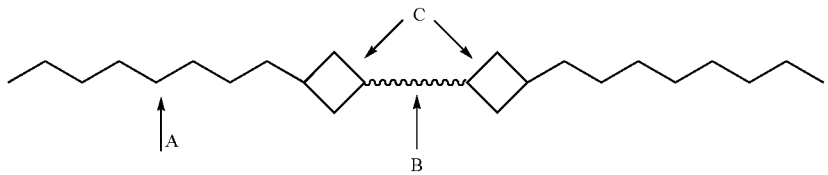

(1) General Structure of a Geminal Zwitterionic Liquid

The geminal zwitterionic liquids are electrically neutral compounds, but possess positive formal charges (cation) and negative (anion) on different atoms of the same molecule. These molecules are able to adapt to different environments and therefore, can be designed to respond efficiently according to the contaminants and operating conditions where they are applied.

The following are examples of chemical structures of zwitterionic liquids which are reported in the literature (2) [Chemistry Letters, 2004, 33 (12), 1594-1595; Latvian Journal of Chemistry, 2010, (1-4), 102-113; Monatshefte für Chemie, 2008, 139, 799-803].

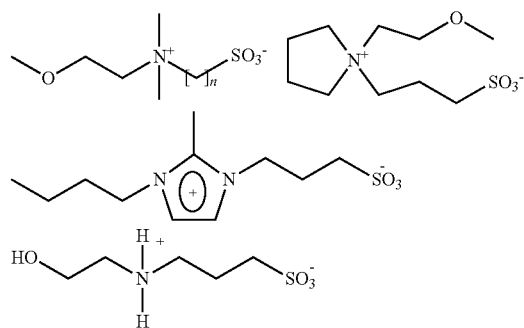

(2) Chemical Structures of Some Zwitterionic Liquids Reported in the Literature

In the particular case of petroleum extraction, is known that, after primary and secondary recovery, the oilfield still contains of the 50 to 80% of the original oil in place. This is because the efficiency of primary and secondary methods of recovery are limited mainly by two factors:

In the scale of the pore, crude oil can reach a sufficiently low residual saturation, to be in the form of discontinuous globules, trapped by capillary forces.

At the scale of the reservoir, there are certain areas during secondary recovery in which the injected fluid does not penetrate due to low permeability of these areas.

The methods currently proposed for enhanced recovery are directed to solving the aforementioned problems and the use of chemicals such as surfactants which modify wettability of reservoir rocks, is one of the methods more widely used. Among these surfactants there are cationic, anionic, nonionic and zwitterionic or mixture thereof.

A wettability modifier is defined as a surfactant capable of changing the affinity of the reservoir rock in a favorably manner for recovery purposes. Wettability is a measure of the interaction between the phases present in the reservoir and is a function of the interfacial chemistry of these phases and determines the tendency of a fluid to move or adhere to a solid surface in the presence of other immiscible fluids. The wettability of a rock can be naturally modified by adsorption of polar compounds, the formation of deposits of organic material that was originally in the oil or by external agents.

These wettability changes affect capillary pressure, relative permeabilities, residual oil saturation and irreducible water saturation.

Despite the continuing advances in the development of wettability modifying chemicals, currently there are reservoirs very difficult to treat, mainly due to the fact that they are naturally fractured, possess low permeability, they have heterogeneous lithologies, high temperatures (over 90° C.) and a high salinity (usually greater than 60,000 ppm as sodium chloride) and high content of divalent ions (calcium and magnesium, greater than 5000 ppm).

Consequently, characterizing the rock type of reservoir, as well as, the composition of the crude oil adsorbed and surrounding environment, is of utmost importance to design new molecular structures of wettability modifiers that are tolerant to saturated salt brines, also they should possess good diffusion through the medium which is generally composed of brine-oil mixture and they must possess polar groups with chemical affinity to the rock in order to change favorably the rock wettability of oil-wet to water-wet.

There are a varied number of chemicals which have been used to solve these problems, among which can be mentioned, anionic surfactants such as alkyl sodium sulphonates or cationic surfactants such as alkyltrimethylammonium chlorides, but unfortunately their application is not universal, due to the particular reservoir conditions around the world. Reservoirs in Mexico are a good example of reservoirs of difficult treatment, which are naturally fractured and of mixed lithology, high temperature and salinity these conditions are completely different to which they have in other countries that is why, it becomes important to develop more versatile chemicals than they can be used in increasingly difficult conditions and also can simultaneously solve the largest number of problems, such as corrosion which is directly associated with the use of sea water or connate water which are usually used as a solvent for the wettability modifier chemicals in order to minimize the costs of their implementation and it can be injected into the oil field.

Some examples of wettability modifying chemicals that have been developed are mentioned below:

The U.S. Pat. No. 5,042,580 (Oil recovery process for use in fractured reservoirs) is related to an enhanced recovery process consisting of injecting into the reservoir a wettability modifier composed of a mixture of different types of surfactant of the type alkyl sulfonate and chromium salts derived from fatty carboxylic acids.

The U.S. Pat. No. 4,509,951 (Enhanced recovery through processes of imbibition) claimed an enhanced recovery process which involves injecting into the reservoir one wettability modifier composed of a mixture of different types of products, such as, ammonium salts, hydroxides of alkali metals, alkyl tripolyphosphates, carbonates and bicarbonates of alkali metal.

The US Patent 2009/0023618 A1 (Oil recovery method) claimed an enhanced recovery process consisting of injecting into the reservoir a wettability modifier integrated of a mixture of different compounds based on organophosphates.

The U.S. Pat. No. 4,842,065 (Oil recovery process using a cyclic process of wettability modification) demanded an enhanced recovery process consisting of injecting into the reservoir a wettability modifier made of a mixture of different types of ethoxylated alcohols.

The U.S. Pat. No. 3,643,738 (Wettability control in recovery processes of Oil) claimed a process that allows to control the wettability change through the use of mixtures of sulfonates derived from petroleum.

The MX Patent 318024 refers to a composition of geminal zwitterionic liquids based on amino acid with wettability modifying properties in processes of enhanced oil recovery, with the following structural formula:

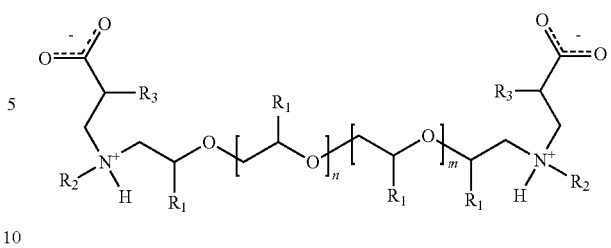

(3) Structural Formula of Geminal Zwitterionic Liquids of the MX Patent 318024

It should be noted that zwitterionic liquids of such request differ from the present invention, by not being type hydroxy propyl betaine, besides they not exhibit simultaneous inhibitory/dispersants properties of asphaltenes.

Furthermore, the phenomenon of the precipitation of asphaltenes within crude oil occurs when, favorable conditions of temperature, pressure and composition promote the association of asphaltene molecules to generate nanoaggregates which can grow and produce large and heavy aggregates of asphaltenes that become separated from the hydrocarbon medium.

The magnitude of the dimensions of asphaltene aggregates produces their migration to the bottom of the reservoir, the pipe or any equipment whereas their polar nature generates a strong adherence to the surface of the aforementioned surfaces. This phenomenon is known by the name of asphaltene deposition.

The deposition of asphaltene is directly related to: 1) The formation damage within petroleum reservoirs;

2) The fouling and plugging of production wells and transportation pipelines of petroleum and hydrocarbon derivatives;

and, 3) The fouling that occurs in refinery plants of crude oil.

These issues cause great economic losses annually to the oil industry.

Traditionally in the oil industry, the fouling and clogging problems occasioned by asphaltenes deposition have been controlled through the use of inhibitors and/or asphaltenes dispersants; whose molecular structure is constituted by two essential parts known as head- and tail-group.

There are many reports in the literature related to the application of chemicals to inhibit or disperse asphaltene deposits, for example: U.S. Pat. No. 7,122,113 B2; U.S. Pat. No. 7,122,112 B2; U.S. Pat. No. 7,097,759 B2; U.S. Pat. No. 6,946,524 B2; U.S. Pat. No. 6,313,367 B1; U.S. Pat. No. 6,204,420 B1; U.S. Pat. No. 6,180,683 B1; U.S. Pat. Nos. 6,063,146; 6,048,904; 5,504,063; 5,494,607; 5,466,387; 5,388,644 and 5,021,498; MX 287535 patents and the request US 2011/0162558 A1.

The U.S. Pat. No. 7,122,113 B2 refers to the use of dendrimeric compounds to solubilize asphaltenes present in a hydrocarbon blend. Preferably the dendrimer compound is a hyperbranched poly(ester-amide) preferentially constructed from succinic anhydride, diisopropanolamine and functionalized with polyisobutenyl succinic anhydride.

The U.S. Pat. No. 7,122,112 B2 refers to the development of compounds of the structural formula:

(4)

that specifically contains within its structure, carboxyl- and amide-groups; and its implementation as asphaltene dispersant in crude oil. In the structural formula (4), $R_5$ is a dysfunctional alkyl group which can vary from $C_1$ a $C_{70}$ y $R_3$ y $R_4$ are independent radicals that can be represented by the groups aryl, alkyl, alkylaryl, heterocyclyl or hydrogen. The patent also indicates that these compounds increases desemulsification, reduces the viscosity, the sediments formation, fouling of surfaces and the corrosion.

U.S. Pat. No. 7,097,759 B2 refers to the development of compounds of the structural formula:

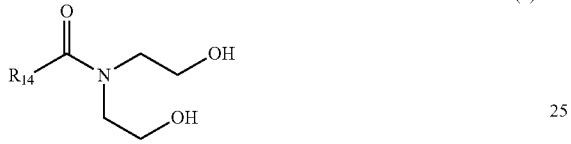

(5)

which specifically contains within of their structure a carbonyl-, thiocarbonyl- or imine group and its application as asphaltene dispersant in crude oil. In structural formula (5), $R_{14}$ is an alkyl group that can vary from $C_{15}$ to $C_{21}$. The patent also indicates that these compounds increase desemulsification, reduce viscosity as well as sediment formation. Fouling of surfaces and corrosion are also claimed to be reduced.

U.S. Pat. No. 6,946,524 B2 refers to a process for producing polyester-amides, by reacting an polyisobutylene with a first agent selected from the group consisting of monounsaturated acids having of 3 to 21 carbon atoms and derived from them, and a second agent selected from the group consisting of monoethanolamine and alkylamines of structural formula:

where R represents an alkyl group having of 1 to 4 carbon atoms. The polyester-amides produced are used both as stabilizing asphaltenes in crude oil as well as in products derived from crude oil.

U.S. Pat. No. 6,313,367 B1, mentions that various esters and reaction products of ethers are excellent asphaltene inhibitors or dispersants and can be used in hydrocarbons such as crude oil. The asphaltene inhibitors can be 1) esters formed from the reaction of polyhydric alcohols with carboxylic acids, 2) ethers formed from the reaction of glycidyl ethers or epoxides with polyhydric alcohols and 3) esters formed from the reaction of glycidyl ethers or epoxides with carboxylic acids.

U.S. Pat. No. 6,204,420 B1, mentions the development of a new formulation in which the asphaltene dispersant action of carboxylic acids can be greatly enhanced by the addition of small amounts of esters which are derived from alkylphosphoric acids.

The formulation is composed of: A) 5 to 99 wt. % of a carboxylic acid, having more than 4 carbon atoms, an ether-carboxylic acid possessing substituents such as alkyl of $C_{18}$-$C_{22}$, alkenyl of $C_{18}$-$C_{22}$, or alkylaryl of $C_6$-$C_{18}$; a carboxylic amide acid or a mixture of them and B) 1 to 95 wt. % of a phosphoric mono- or diester or a mixture of them, which is substituted by an alkyl group of $C_{18}$-$C_{22}$; an alkenyl of $C_{18}$-$C_{22}$, an alkylaryl of $C_6$-$C_{18}$ or alkoxylated. Where the sum of A and B is 10 wt. %.

The MX patent 287535 and the US patent application 2011/0162558 A1, refers to the use of additive formulations possessing asphaltene inhibitor/dispersant properties. These formulations are based in oxazolidines, which are derived from polyalkyl or polyalkenyl N-hydroxyalkyl succinimides, with the following structural formula:

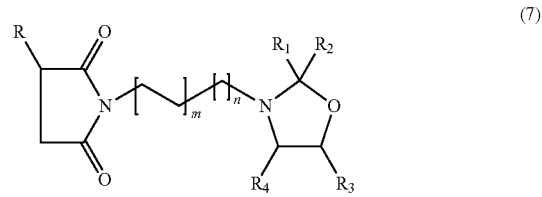

(7)

From the above, it is important to remark that in none of the aforementioned references, is referred the use of geminal zwitterionic liquids based on hydroxypropyl betaine to control asphaltene deposition neither it is suggested their obtaining process. It can be observed that none of the aforementioned references claim the use of geminal zwitterionic liquids based on hydroxypropyl betaine to modify favorably the rock wettability within a petroleum reservoir during the execution of enhanced recovery processes of crude oil in a wide range of rocks such as limestone, dolomite, sandstone, quartz or heterogeneous lithologies, where these geminal zwitterionic liquids may be exposed to brines with high content of divalent ion as they are calcium, magnesium, barium and strontium (150,000 ppm), temperatures up to 220° C.; pressures up to 300 kg/cm²; and they prevent and control the asphaltenes precipitations in pipeline of crude oil production in enhanced oil recovery processes.

BRIEF DESCRIPTION OF THE DRAWINGS

In order to have a better understanding regarding this patent application about geminal zwitterionic liquids based on hydroxypropyl betaines, production process and use as wettability modifiers with asphaltenes inhibitory/dispersant properties, a brief description of Figures included is presented:

The FIG. 1 shows the production of oil in the Amott cell capillary for: a) Reference and b) Product 1.

Figure 1:
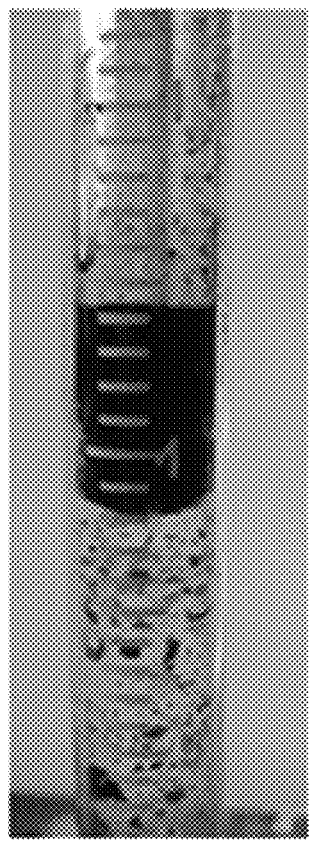
Figure 1:
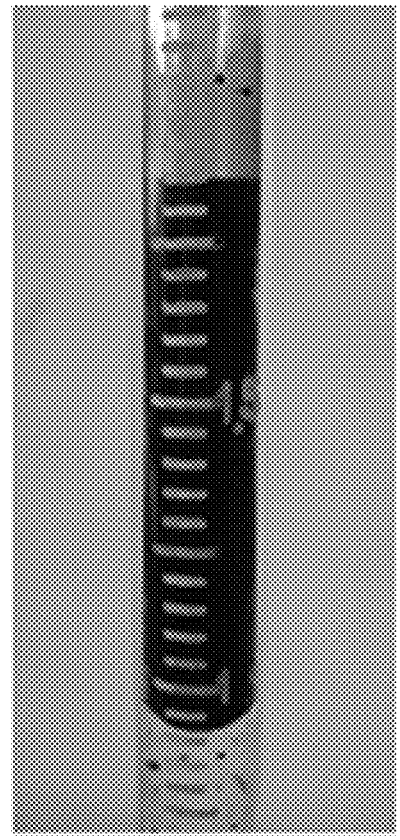
Figure 2:
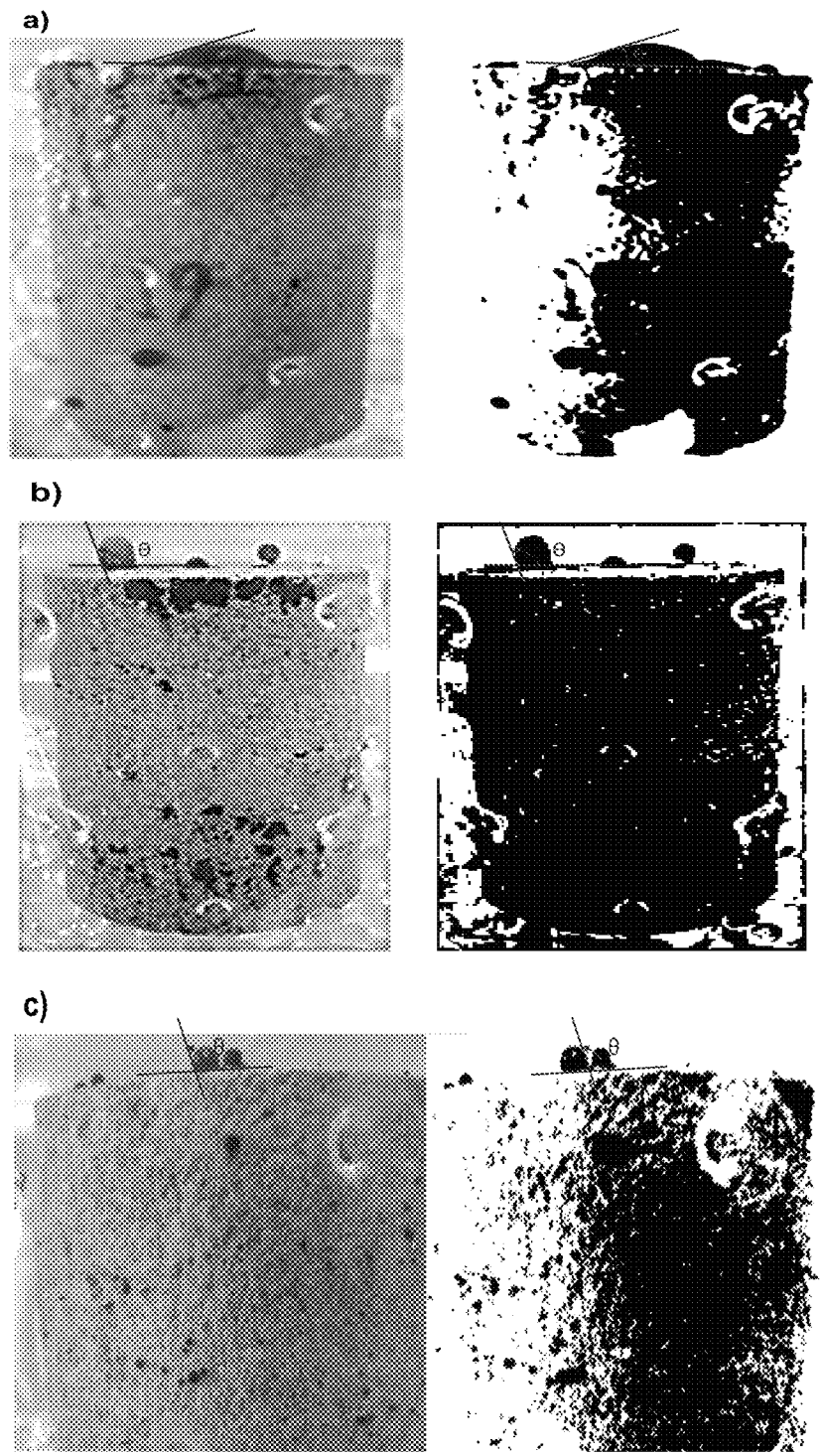

The FIG. 2 shows the contact angle for: a) system that only contains brine, b) a system containing brine and 300 ppm of product 1, c) system containing brine and 300 ppm of product 2.

Figure 3:
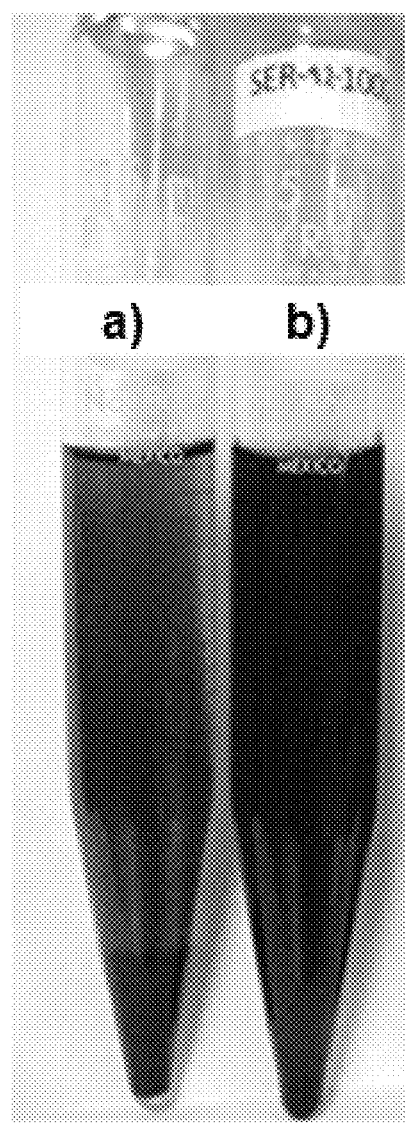

The FIG. 3 shows asphaltenes precipitated from reference (a) and the dispersant activity to the product 2 (b).

DETAILED DESCRIPTION OF THE INVENTION

The present invention relates to obtaining and use of zwitterionic geminal liquids based on hydroxypropyl betaines, as effective rock wettability modifiers on limestone, dolomite, sandstone, quartz or heterogeneous lithologies in presence of crude oil and brine with high content of divalent ions such as calcium, magnesium, barium and strontium, high temperature and high pressure in enhanced oil recovery processes.

The zwitterionic geminal liquid based on hydroxypropyl betaine of the present invention have also the property of acting as inhibitors/dispersants of asphaltenes in extraction and production operations, thereby enabling, preventing and controlling properly the asphaltene precipitation problems. An additional advantage presented by the zwitterionic liquids of the present invention is that due to its molecular structure, they may be soluble in brine, crude oil or organic solvents such as toluene, xylenes, chloroform and alcohols. So they offer operational advantages for field application.

The present invention is the first one related to a family of chemical compounds that exhibit simultaneously wettability modification properties and inhibition-dispersion of asphaltenes.

The zwitterionic geminal liquid based on hydroxypropyl betaines of the present invention have the following structural formula (8):

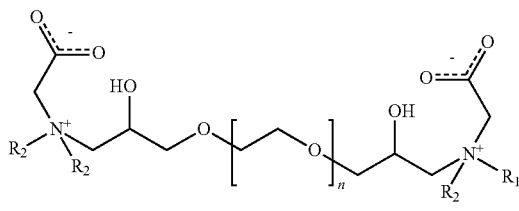

(8)

where:
- $R_1$=Is a alkyl or alkenyl chain, linear or branched, preferably of 1 to 30 carbon atoms; or a cycle alkyl or aryl group, preferably of 5 to 12 carbon atoms;
- $R_2$=Is hydrogen or a alkyl or alkenyl chain, linear or branched, preferably of 1 to 30 carbon atoms; or an cyclo alkyl or aryl group, preferably of 5 to 12 carbon atoms;
- n=has values from 1 to 500 depending on the molecular weight of the poly(ether) used, whose molecular weight is in the range of 100 to 22,000 g/mol.

For the development of the present invention, it follows a process which consists of the following steps: 1) Synthesis and characterization of zwitterionic geminal liquid based on hydroxypropyl betaine; and 2) Experimental evaluation of the wettability modifier and inhibitory/dispersants of asphaltene properties.

1) Synthesis and Characterization of Zwitterionic Geminal Liquid Based on Hydroxypropyl Betaines.

The zwitterionic geminal liquids based hydroxypropyl betaine, object of the present invention, are prepared according to synthesis scheme (9), and comprises two reaction steps:

The first stage comprises in doing react polyethyleneglycol diglycidyl ether of formula I which possess two epoxide groups, one at the end and the other at the beginning of the polymeric chain, and whose molecular weight is in the range of 100 to 22.000 g/mol; with amines of formula II, where $R_1$ and $R_2$ may be alkyl or alkenyl chain, linear or branched, preferably of 1 to 30 carbon atoms; or cycle alkyl or aryl groups, preferably of 5 to 12 carbon atoms and where in $R_2$ can also be hydrogen.

The reaction is carried out in a molar ratio between the compounds of formula I and II of 1:1.5 to 1:4, respectively, even if a molar ratio of 1:1.8 to 1:2.6 is preferred. The reaction is carried out in the absence of solvent or in the presence of solvents such as acetonitrile, dioxane, chloroform, dimethylformamide, dimethylsulfoxide, acetone or short chain alcohols; in a reaction time of 6 to 48 hours, preferably 12 hours, and at a temperature of 50 to 150° C.; to obtain the amino alcohols of formula III.

The second step of obtaining process consists in the reaction between the amino alcohol of formula III and alpha halogenated acids, such as, chloro or bromoacetic acid or its sodium or potassium salts of formula IV, in a molar ratio of 1:1.5 to 1:4, preferably 1:1.8 to 1:2.6. The reaction is carried out in the presence of solvents such as water, dioxane, alcohols, or aromatics or hydrocarbon, preferably water. The reaction time, temperature and pressure depend on the structure of the compounds of formulas III and IV; usually the reaction time varies from 6 to 48 hours, preferably of 12 to 24 hours, the temperature from 40 to 180° C., preferably of 80 to 130° C., and the pressure is generally atmospheric, for obtaining the zwitterionic geminal liquid based on hydroxypropyl betaine of formula V.

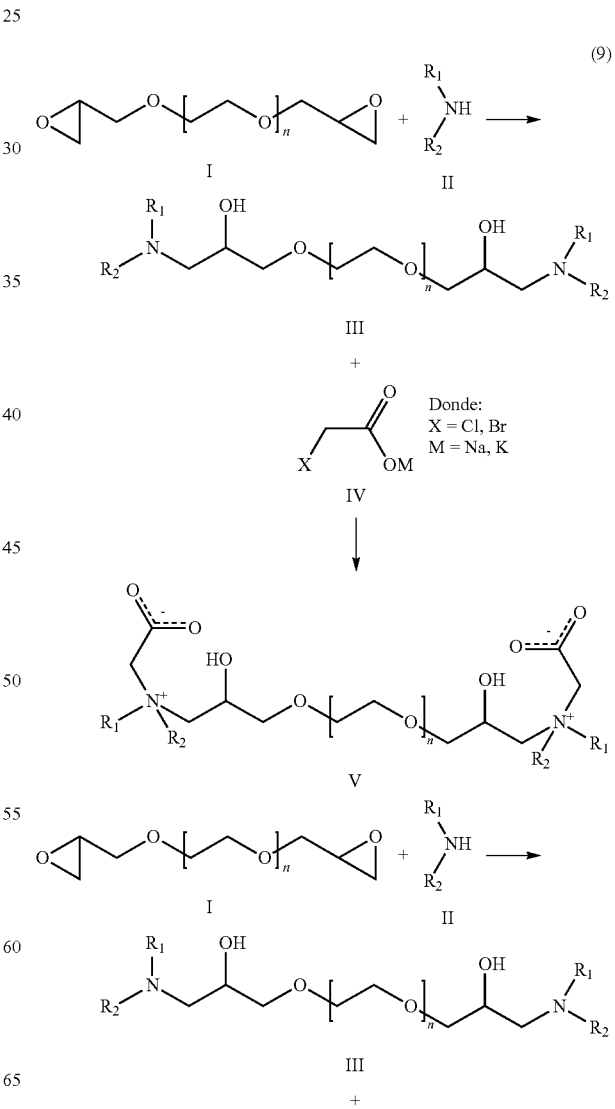

(9)

-continued

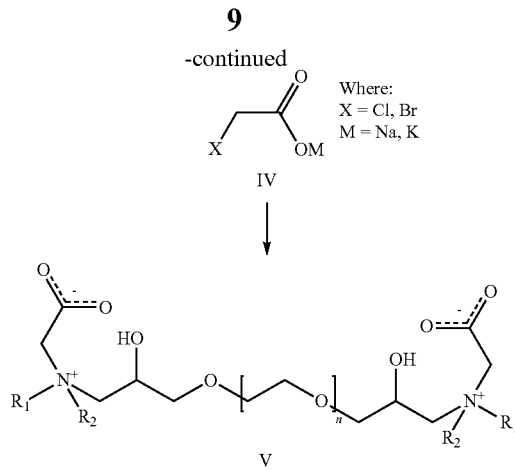

Where:
X = Cl, Br
M = Na, K

Here some examples of the obtaining of zwitterionic geminal liquid based hydroxypropyl betain are described for a better understanding of the present invention, without this limiting its scope.

Example 1

Preparation of Zwitterionic Geminal Liquid Based on Hydroxypropyl Betaine (Product 1)

First Stage.

In a round flask of 25 ml equipped with a condenser, magnetic stirrer, heating mantle and thermometer, were placed 4 g of dioctylamine and 4.79 g of poly (ethylene glycol) diglycidyl ether (PEGDE).

The mixture of reagents was subjected to vigorous agitation and its temperature will increased to a range of 100-105° C., under these conditions the mixture was continuously stirred for 6 hrs. Once the reaction time was consumed, the reaction crude was characterized by spectroscopic methods to know its composition, so it was determined the obtaining of 9.1 g of bis N,N-dioctyl hydroxy polyether as a transparent yellowish appearance and viscous liquid.

Second Stage.

In a round flask of 25 mL instrumented with a condenser, magnetic stirrer, blanket heater and thermometer, were placed 9.1 g of bis-N,N-dioctyl hydroxy-N-polyether of product and a solution of 2.1 g of sodium chloroacetate in 30 g of H$_2$O. The reaction mixture was subjected to vigorous stirring and reflux for a period of 24 hours.

Once the reaction time was consumed, it was carried out a chloroform extraction of the organic phase. The chloroform phase was filtered and evaporated under reduced pressure, obtaining 8.6 g of clear orange liquid called bis N,N-dioctyl-N-polyether hydroxy betaine (Product 1).

The spectroscopic characteristics of the Product 1 are as follows:

Representative IR bands (cm$^{-1}$): 3266, 2923, 2860, 1736, 1627, 1459 y 1097.

Representative NMR chemical shifts of $^1$H (CDCl3), 200 MHz, δ (ppm):

3.83, 3.56, 3.10, 2.90 y 0.79.

Representative NMR chemical shifts of $^{13}$C (CDCl$_3$), 50 MHz, δ (ppm):

178.5, 70.2, 64.7, 61.8, 57.7, 53.9, 31.4, 22.3 y 13.8.

Example 2

Preparation of the Zwitterionic Geminal Liquid Based on Hydroxypropyl Betaine (Product 2).

First Stage.

In a round flask of 25 ml equipped with a condenser, magnetic stirrer, heating mantle and thermometer, 3 g of didodecylamine and 5.79 g of poly (ethylene glycol) diglycidyl ether (PEGDE) were placed.

The mixture of reagents was subjected to vigorous agitation and its temperature was increased to a range of 100-105° C., under these conditions it was continuously stirred for 6 hrs.

Once the reaction time was consumed, the reaction crude was characterized by spectroscopic methods to know its composition, so 9.1 g of bis N,N-didodecyl hydroxy polyether, were obtained as a transparent yellowish appearance and viscous liquid.

Second Stage.

In a round flask of 25 ml, instrumented with a condenser, magnetic stirrer, blanket heater and thermometer, were placed 9.1 g of the bis-N,N-didodecyl hydroxy-N-polyether product and a solution of 1.8 g of sodium chloroacetate in 10 g of H$_2$O and 20 g of dioxane. The reaction mixture was subjected to vigorous stirring at reflux temperature for a period of 48 hours.

Once the reaction time was consumed it was carried out a chloroform extraction of the organic phase.

The chloroform phase was filtered and evaporated under reduced pressure obtaining 8.2 g of clear orange liquid called bis N,N-didodecyl-N-polyether hydroxy betaine (Product 2).

The spectroscopic characteristics of the product 2 are as follows:

Representative IR bands (cm-1): 3271, 2921, 2858, 1729, 1625, 1454 y 1098.

Representative NMR chemical shifts of $^1$H (CDCl3), 200 MHz, δ (ppm):

3.85, 3.53, 3.11, 2.91 y 0.77.

Representative NMR chemical shifts of $^{13}$C (CDCl3), 50 MHz, δ (ppm):

178.2, 70.1, 64.3, 61.5, 57.3, 53.2, 31.1, 22.3 y 13.5.

2) Experimental Evaluation of the Wettability Modifier Properties and Inhibitory/Dispersants of Asphaltene.

a) Performance Testing of Zwitterionic Geminal Liquid Branched Based on Hydroxypropyl Betaine as Wettability Modifiers.

For the evaluation of wettability modifier properties of zwitterionic geminal liquids of the present invention on limestone rocks, dolomite, sandstone, quartz or heterogeneous lithologies, in the presence of brines with high content of divalent ions like calcium, magnesium, barium and strontium, the recovery factor was determined by spontaneous imbibition process using limestone cores within Amott cells, in order to evaluate the wettability modifiers efficiency of the present invention with respect to a reference system without the presence of chemical.

For the evaluations bedford limestone cores were selected, these are mainly composed of calcium carbonate, for being a rock which presents strong adsorption of polar organic compounds of oil and therefore is the most severe case for wettability modifier, whereby it is ensured that this type of chemicals would function adequately in other rock with less tendency to be oil-wet. Coming up next it is described the test method.

Determination of the Recovery Factor for Spontaneous Imbibition Process of Limestone Cores within Amott Cells.

The test method consists in measuring the amount of crude oil recovered from carbonate rock cores initially saturated with oil, due to the spontaneous imbibition processes by water; within Amott cell at constant temperature and atmospheric pressure.

The elements required for the test are:

Amott cell

Recirculation system of controlled temperature.

Limestone core with 3.81 cm of diameter×7 cm of long with permeabilities and porosities known.

Digital Camera

Crude oil

High salinity brine.

Analytical balance.

Soxhlet extractor.

Volumetric glassware

Convection oven

Test Procedure:

1) The carbonate rock cores (limestone or dolomite) .undergo hydrocarbon extraction processes with different organic solvents in a Soxhlet system.

The extraction processes are carried out continuously, sequenced and refluxed; using as solvents: a) Xylene b) Chloroform, c) Methanol, d) Xylene e) Chloroform, f) and g Methanol) Xylene.

The duration of each extraction stage is one day and the total process time is 7 days.

2) Determine the absolute permeability of the cores to the helium, as well as their effective porosity.

3) Dry the cores in an oven at 100° C. and record the weight.

4) Put in contact the cores with dead oil that coming of the reservoir of interest, during 5 days at the temperature of interest and a pressure of 140±5 psi, in a high pressure cell.

5) The impregnated cores were let to drain at room temperature and atmospheric pressure, until no dripping was observed. The process takes about 12 hours and for this, use is made of a wire mesh (number 200).

6) Weigh the impregnated cores with dead oil and obtain by weight difference the amount of oil adsorbed in porous media.

7) Prepare 500 ml of aqueous solution (brine) to evaluate the concentration of chemical required in the test.

8) Place the impregnated cores with the dead oil within Amott cells and add carefully 350 ml of high salinity brine without chemical and another cell with the solution of the chemical to evaluate to the required concentration.

9) Increase the temperature of the system and keep it for a period of time which is intended to determine the recovery factor under the conditions of temperature and salinity.

10) Quantify the amount of oil produced due to spontaneous imbibition processes of water under the study conditions and determine the recovery factor according to the following equation:

$$F_r = \frac{A_r}{A_{opm}} \times 100$$

where:

$F_r$=Recovery factor; $A_r$=recovered oil; $A_{opm}$=Original oil adsorbed in the porous medium.

11) Photographing the systems to measure the contact angle rock-oil and determine the wettability of the rock in a reference system and chemical systems.

Example 3

Evaluation of a Process of Spontaneous Imbibition by Wettability Change Using a Light Crude Oil.

Following the methodology described above, a carbonated core was placed in Amott cell which were saturated with light oil (whose characteristics are shown in Table 1) and contacted with solutions of the products 1 and 2 in brine 1 (whose characteristics are shown in Table 2).

The experiment had duration of 15 days at 90° C.

In Table 3, are shown the data of recovery obtained in the Amott cells for the products 1, 2 at a concentration of 300 mg/L and for the reference, for this case, brine 1 in which no chemical was added.

From the results of Table 3 it can be seen that the zwitterionic geminal branched liquid based on hydroxypropyl betaine (Products 1 and 2) recover about 1.5 times more than the light crude oil that the reference so they work properly as wettability modifiers in spontaneous imbibition processes.

Also, the results in Table 4 shows how the product has the ability to change the wettability of the rock of the oil-wet (θ=18), as observed in the reference system to water-wet, both as for product 1 (θ=110) as in the case of product 2 (θ=115).

TABLE 1

SARA data analysis, acid and basics number of light oil coming of Poza Rica field.

| oil | SARA | | | | Total acid numer (TAN) | Total basic numer (TBN) |
|---|---|---|---|---|---|---|
| | Saturated | Aromatics | Resins | Asphaltenes | | |
| light oil | 30.68 | 28.62 | 39.35 | 1.32 | 0.21 | 1.7 |

TABLE 2

Physicochemical analysis of the brine 1.

| Physical properties | | |
|---|---|---|
| Temperature | 20° C. | |
| pH | 7.65 | @ 20° C. |
| Density | 1.0043 | g/cm³ @ 20° C. |
| Conductivity | | µS/cm @ 20° C. |
| Turbidity | 4 FTU | |

TABLE 2-continued

Physicochemical analysis of the brine 1.

Chemical properties

| Cations | (mg/L) | (meq/L) | Anions | (mg/L) | (meq/L) |
|---|---|---|---|---|---|
| Sodium (Na$^+$) | 1 703.66 | 74.116 | Chlorides (Cl$^-$) | 3 200.00 | 90.260 |
| Potassium (K$^+$) | — | — | Sulfates (SO$_4^-$) | 350.00 | 7.287 |
| Calcium (Ca$^{++}$) | 416.00 | 20.758 | Carbonates (CO$_3^-$) | 0.00 | 0.00 |
| Magnesium (Mg$^{++}$) | 106.95 | 8.799 | Bicarbonates (HCO$_3^-$) | 405.04 | 6.638 |
| Iron (Fe$^{++}$) | 0.06 | 0.002 | Hidróxides (OH$^-$) | — | — |
| Manganese (Mn$^{++}$) | — | — | Nitrites (NO$_2^-$) | — | — |
| Barium (Ba$^{++}$) | 35.00 | 0.510 | Nitratos (NO$_3^-$) | — | — |
| Strontium (Sr$^{++}$) | — | — | Fosfates (PO$_4^{-3}$) | — | — |
| Total: | 2 261.88 | 104.186 | Total: | 3 955.04 | 104.186 |

Dissolved and suspended solids

| | (mg/L) | | (mg/L) |
|---|---|---|---|
| Total Solids | — | Total Hardness as CaCO$_3$ | 1 480.00 |
| Total Dissolved Solids (TDS) | 6 216.92 | Calcium Hardness as CaCO$_3$ | 1 040.00 |
| Total Suspended Solids (SST) | — | Magnesium Hardness as CaCO$_3$ | 440.00 |
| Fats and Oils | — | Alkalinity to "F" as CaCO$_3$ | 0.00 |
| Soluble Silica | — | Alkalinity to "M" as CaCO$_3$ | 332.00 |
| Ferric Oxide | — | Salinity as NaCl | 5 275.00 |
| Acidity as | — | Stability Index | 0.288 10 |
| | | Trend | encrusting |

TABLE 3

Results of light oil recovery in Amott cells.

| Product | Porosity of limestone core (%) | Limestone core permeability to helium (mD) | Oil impregnated (g) | Total oil recovered (g) | Recovery percentage (%) |
|---|---|---|---|---|---|
| Reference | 19.6 | 118 | 12.2874 | 4.5796 | 37.27 |
| 1 | 20.0 | 115 | 11.7692 | 6.2252 | 52.89 |
| 2 | 19.5 | 112 | 11.8990 | 6.3124 | 53.05 |

In Table 4, is observed the contact angle values rock-oil and the rock wettability obtained in Amott cells, for the products 1 and 2 at a concentration of 300 mg/L and for the reference system; in this case brine 1 without additive.

TABLE 4

Results of contact angle for rock-oil system and wettability of the rock in Amott cells for light oil experiments.

| Product | Contact angle θ rock-oil (°) | Rock wettability |
|---|---|---|
| Reference | 18 | Oil-wet |
| 1 | 110 | Water-wet |
| 2 | 115 | Water-wet |

Example 4

Evaluation of a Spontaneous Imbibition Process by Wettability Change Using a Heavy Crude Oil.

According the aforementioned methodology described above, carbonate cores were placed in Amott cells, which were saturated with heavy oil and they were put in contact with the products of solutions 1 and 2 in the brine 2 at a concentration of 300 mg/L.

The characteristics of the heavy crude oil and the brine 2 are shown in Tables 5 and 6, respectively.

TABLE 5

ESARA data analysis, total acid and basics number of heavy oil.

| | SARA | | | | Total acid numer (TAN) | Total basic numer (TBN) |
|---|---|---|---|---|---|---|
| oil | Saturated | Aromatics | Resins | Asphaltenes | | |
| heavy oil | 13.4 | 24.76 | 51.01 | 10.44 | 1.83 | 2.12 |

TABLE 6

Physicochemical analysis of the brine 2.

Physical properties

| Temperature | 20° C. | |
| pH | 6.68 | @ 20° C. |
| Density | 1.0216 | g/cm$^3$ @ 20° C. |
| Conductivity | 45 600 | μS/cm @ 20° C. |
| Turbidity | 15 FTU | |
| Color | 18 Pt-Co | |

TABLE 6-continued

Physicochemical analysis of the brine 2.

Chemical properties

| Cations | (mg/L) | (meq/L) | Anions | (mg/L) | (meq/L) |
|---|---|---|---|---|---|
| Sodium (Na$^+$) | 11 630.06 | 505.907 | Chlorides (Cl$^-$) | 22 000.00 | 620.540 |
| Potassium (K$^+$) | — | — | Sulfates (SO$_4^-$) | 825.00 | 17.177 |
| Calcium (Ca$^{++}$) | 1 976.00 | 98.603 | Carbonates (CO$_3^-$) | 0.00 | 0.00 |
| Magnesium (Mg$^{++}$) | 427.86 | 35.197 | Bicarbonates (HCO$_3^-$) | 122.00 | 1.999 |
| Iron (Fe$^{++}$) | 0.25 | 0.009 | Hidróxides (OH$^-$) | — | — |
| Manganese (Mn$^{++}$) | — | — | Nitrites (NO$_2^-$) | — | — |
| Barium (Ba$^{++}$) | — | — | Nitrates (NO$_3^-$) | — | — |
| Strontium (Sr$^{++}$) | — | — | Fosfates (PO$_4^{-3}$) | — | — |
| Total: | 14 034.41 | 639.716 | Total: | 22 947.00 | 639.716 |

Dissolved and suspended solids

| | (mg/L) | | (mg/L) |
|---|---|---|---|
| Total Solids | — | Total Hardness as CaCO$_3$ | 6 700.00 |
| Total Dissolved Solids (TDS) | 36 981.41 | Calcium Hardness as CaCO$_3$ | 4 940.00 |
| Total Suspended Solids (SST) | — | Magnesium Hardness as CaCO$_3$ | 1 760.00 |
| Fats and Oils | — | Alkalinity to "F" as CaCO$_3$ | 0.00 |
| Soluble Silica | — | Alkalinity to "M" as CaCO$_3$ | 100.00 |
| Ferric Oxide | — | Salinity as NaCl | 36 265.59 |
| Acidity as | — | Stability Index | −0.71714 |
| | | Trend | encrusting |

Table 7, contains the obtained results in the Amott cell with carbonate cores in contact with solutions of zwitterionic geminal liquid type hydroxypropyl betaine (Products 1 and 2) at a concentration of 300 mg/L in the brine 2 and using heavy crude oil.

TABLE 7

Results of heavy oil recovery in Amott cells.

| Product | Porosity of limestone core (%) | Limestone core permeability to helium (mD) | Oil impregnated (g) | Total oil recovered (g) | Recovery percentage (%) |
|---|---|---|---|---|---|
| Reference | 19.4 | 108 | 6.8124 | 0.8364 | 12.28 |
| 1 | 19.6 | 113 | 6.6515 | 2.0207 | 30.38 |
| 2 | 19.2 | 115 | 6.4726 | 1.705 | 26.34 |

From the results of Table 7 we can see that the zwitterionic geminal liquid branched based on hydroxypropyl betaine (Products 1 and 2) recover more than double of heavy crude oil that the reference, so that, they function adequately as wettability modifiers in spontaneous imbibition processes.

b) Evaluation of the Inhibiting/Dispersant Activity of Asphaltene of the Zwitterionic Geminal Liquid Branched Based on Hydroxypropyl Betaine in a Heptane-Solution Blend of Asphaltenes in Toluene by UV-Visible Spectroscopy.

This test is based on the fact that the asphaltenes are soluble in aromatic hydrocarbons but insoluble in aliphatic hydrocarbons such as n-heptane.

The dispersing capability of the zwitterionic geminal liquid branched based on hydroxypropyl betaine can be evaluated by dissolving the asphaltenes in toluene and then adding n-heptane to produce precipitation.

Since the asphaltenes absorb energy in the UV-visible spectrum, you can have a proportional measure of asphaltene precipitated by measuring the absorption in the UV-visible spectrum of the resulting supernatant liquid.

Experimental Methodology.

The procedure which has been designed specifically for this test consists on:

Preparing a solution of 5000 ppm of asphaltenes in toluene.

Preparing a solution of 5000 ppm of the zwitterionic liquid branched based hydroxypropyl betaine in toluene.

In a test tube with conical bottom add 1 ml of the asphaltenes in toluene solution, 2 ml of a solution of zwitterionic liquid based hydroxypropyl betaine in toluene and 7 ml of n-heptane, to obtain 1000 ppm of the zwitterionic liquid based hydroxypropyl betaine in solution, shake vigorously for 1 minute and allow to stand for 24 hours.

Prepare the reference: Add to a test tube with conical bottom 1 ml of solution of asphaltenes in toluene, 2 ml of toluene and 7 ml of n-heptane, shake vigorously and allow to stand for 24 hours.

After the standing time, is collected 1 ml of the supernatant both of the test tube as well as the reference tube (being careful not to take the asphaltene settled at the bottom) and each are diluted with 4 ml of toluene and stirred vigorously.

The diluted supernatants were analyzed by UV-visible spectrophotometry at a wavelength of 410 nm using toluene as test target. In this manner the absorbance value is obtained so much as to problem sample as well as the reference.

The dispersant activity is indicated as a percentage increase of the dispersed asphaltenes in the sample relative to the dispersed asphaltenes in the reference and is calculated by the following equation:

$$\text{Dispersing activity} = \frac{A_p - A_r}{A_r} \times 100$$

where $A_p$ is the absorbance of the problem sample and $A_r$ is the absorbance of the reference, measurements at 410 nm.

Example 5

Evaluation of the Dispersant Activity of Asphaltene of Zwitterionic Liquid Based Hydroxypropyl Betaine.

Following the methodology described above, the dispersant activity of the products 1 and 2 at a concentration of 1000 mg/l was evaluated.

The results are shown in Table 8 below.

| Product | Absorbance@410 nm | Dispersant activity (%) |
|---|---|---|
| Reference | 0.39 | — |
| 1 | 0.55 | 41.02 |
| 2 | 0.96 | 146.15 |

1.

From the results of Table 8 it is observed that for both products increase the amount of asphaltenes dispersed in the precipitating medium with respect to the reference. It is also observed that the product 2 has a higher dispersant activity regarding to product 1.

What is claimed is:

1. A zwitterionic geminal liquid based on hydroxypropyl betaine, having the following structural formula:

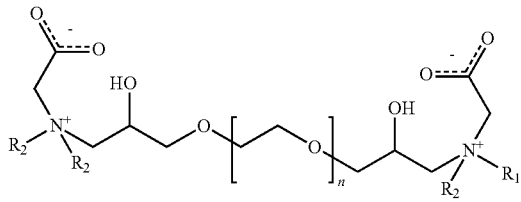

where:
$R_1$ is a linear or branched alkyl chain of 1 to 30 carbon atoms;
$R_2$ is a linear or branched alkyl chain of 1 to 30 carbon atoms; and
n has values from 1 to 500.

2. A process for the obtaining of zwitterionic geminal liquids based on hydroxypropyl betaine, pursuant to claim 1, characterized by the following synthesis scheme:

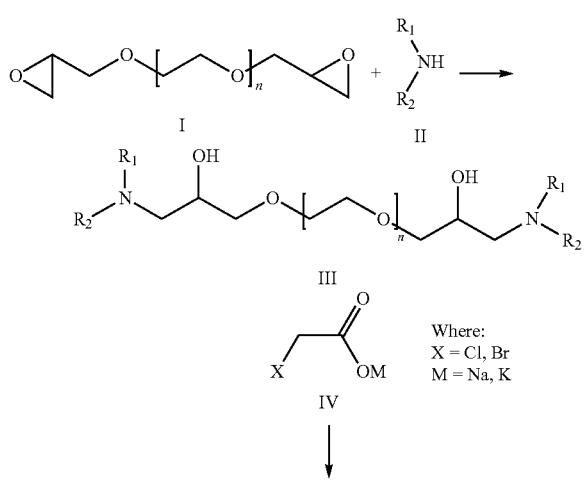

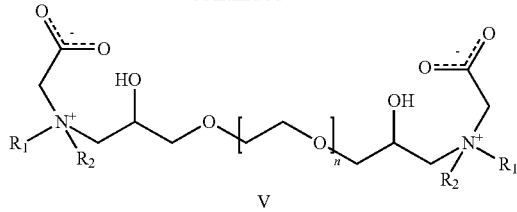

which comprises two reaction steps: the first stage consists of reacting polyethylene glycol diglycidyl ether of the formula I, with primary or secondary amines of formula II; the second stage consists of reacting the aminoalcohols of the formula III with salts of alpha-halogenated acid of formula IV, so as to obtain zwitterionic liquid based hydroxypropyl betaine of the formula V.

3. The process of claim 2, wherein the polyethylene glycol diglycidyl ether of formula I are derived from ethylene oxide.

4. The process of claim 3, wherein the polyethylene glycol diglycidyl ether of formula I contain two epoxy groups, one in the end and the other at the beginning of the polymer chain.

5. The process of claim 2, wherein the average molecular weight of the polyethylene glycol diglycidyl ether of the formula I are in the range of 100 to 22,000 g/mol.

6. The process of claim 2, wherein the reaction is carried out between compounds of formula I and II with a molar ratio value from 1:1.5 to 1:4, respectively.

7. The process of claim 2, where in the secondary amines of formula II, $R_1$ is a linear or branched alkyl chain of 1 to 30 carbon atoms, and $R_2$ is a linear or branched alkyl chain of 1 to 30 carbon atoms.

8. The process of claim 2, wherein the reaction for obtaining of the aminoalcohols of formula III is carried out in the absence or presence of solvents such as acetonitrile, dioxane, chloroform, dimethylformamide, dimethylsulfoxide, acetone or short chain alcohols.

9. The process of claim 2, wherein the reaction for the obtaining of the aminoalcohols of the formula III is carried out in a reaction time from 6 to 48 hours.

10. The process of claim 2, wherein the reaction for the obtaining of the aminoalcohols of formula III is carried out at a temperature of 50 to 150° C.

11. The process of claim 2, wherein the reaction between the compounds of formula III and the alpha halogenated acid or their salts of the formula IV is carried out with a molar ratio of 1:1.5 to 1:4.

12. The process of claim 2, wherein the salt of alpha halogen acid selected is sodium chloroacetate.

13. The process of claim 2, wherein the reaction for obtaining of the compounds of formula V is carried out in the absence or presence of solvents such as water, dioxane, alcohols, aromatic or hydrocarbon.

14. The process of claim 2, wherein the reaction time varies from 6 to 48 hours.

15. The process of claim 2, wherein the temperature is of 40 to 180° C.

16. The process of claim 2, wherein the pressure is generally atmospheric, which varies from 585 to 760 mmHg.

17. A method for modifying the wettability of reservoir rocks such as limestone, dolomite, sandstone, quartz or lithologies heterogeneous, comprising the use of the zwitterionic geminal liquids of claim 1 in order to increase oil recovery in processes of enhanced oil recovery.

18. The method of claim 17, wherein the enhanced oil recovery process is under conditions of high salt content and divalent ions like calcium, magnesium, barium and strontium.

19. The method of claim 17, wherein the temperature is up to 220° C.

20. The method of claim 17, wherein the pressure is up to 8000 psi.

21. The method of claim 17, wherein the salt concentration is up to 400,000 ppm.

22. The method of claim 17, wherein the divalent ion concentration is up to 180,000 ppm.

23. The method of claim 17, wherein the concentration of the zwitterionic liquid to inject for modifying the wettability of oil rock is in concentrations of 25 to 40,000 ppm.

24. The method of claim 23, wherein the concentration to be injected is from 500 to 10,000 ppm.

25. The method of claim 23, where zwitterionic geminal liquids are able to simultaneously inhibit and disperse of asphaltenes.

26. The method of claim 25, wherein the concentration to be injected of zwitterionic liquid for inhibit and disperse asphaltenes is of 25 to 40,000 ppm.

27. The method of claim 26, wherein the concentration to be injected is from 500 to 10,000 ppm.

* * * * *

UNITED STATES PATENT AND TRADEMARK OFFICE
CERTIFICATE OF CORRECTION

PATENT NO. : 10,442,981 B2
APPLICATION NO. : 14/944150
DATED : October 15, 2019
INVENTOR(S) : Violeta Yázmin Mena Cervantes et al.

It is certified that error appears in the above-identified patent and that said Letters Patent is hereby corrected as shown below:

In the Claims

In Claim 1, Column 17, Lines 30-37, the formula currently reads:

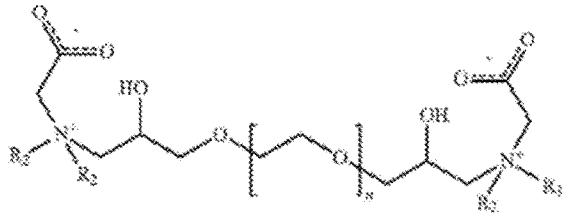

However, it should read:

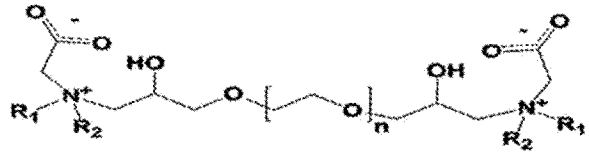

In Claim 2, Column 17, Lines 59-67, the formula currently reads:

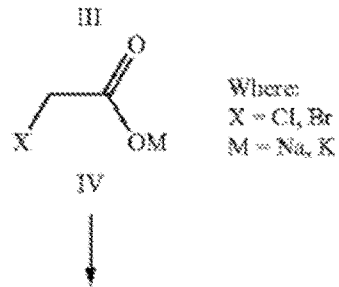

Signed and Sealed this
Fifteenth Day of December, 2020

Andrei Iancu
*Director of the United States Patent and Trademark Office*

CERTIFICATE OF CORRECTION (continued)
U.S. Pat. No. 10,442,981 B2

However, it should read:

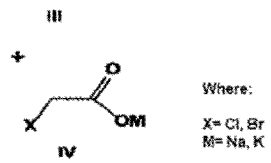

Where:
X= Cl, Br
M= Na, K